US00PP20235P3

(12) United States Plant Patent
Barfield

(10) Patent No.: US PP20,235 P3
(45) Date of Patent: Aug. 25, 2009

(54) EXOTIC ORCHID 'WHITE KNIGHT'

(50) Latin Name: *EXOTIC ORCHID*
Varietal Denomination: White Knight

(76) Inventor: Robert Glen Barfield, P.O. Box 1299, Kea'au, HI (US) 96749

( * ) Notice: Subject to any disclaimer, the term of this patent is extended or adjusted under 35 U.S.C. 154(b) by 298 days.

(21) Appl. No.: 11/784,760

(22) Filed: Apr. 10, 2007

(65) Prior Publication Data

US 2008/0256673 P1 Oct. 16, 2008

(51) Int. Cl.
*A01H 5/00* (2006.01)

(52) U.S. Cl. ..... Plt./311

(58) Field of Classification Search ..... Plt./311
See application file for complete search history.

*Primary Examiner*—Annette H Para

(57) ABSTRACT

A new variety of orchid plant of the Oncidiinae Intergeneric group, *Brassidium,* named EXOTIC ORCHID 'White Knight', distinguished in part by a compact size, highly contrasted flower, and growing quickly from in-vitro culture to flowering.

2 Drawing Sheets

Latin name of the genus and grex of the plant claimed: The Latin name of the genus and grex of the plant claimed is *Brassidium Golden Gamine* 'White Knight' to be identified in the trade as, EXOTIC ORCHID 'White Knight'.

Variety denomination: The present invention is comprised of a new and distinct cultivar of Oncidiinae orchid, and hereinafter referred to by the cultivar name EXOTIC ORCHID 'White Knight'.

BACKGROUND OF THE INVENTION

Oncidiinae comprises a genus of approximately 2000 species from the tropical and subtropical Americas. Oncidiinae are primarily epiphytic or lithophytic with a minor portion being terrestrial. All species are sympodial in growth and may vary greatly in other morphology and size.

Oncidiinae breeding is typically done from sexual methods. Asexual propagation of Oncidiinae is often done in aseptic tissue culture from apical and/or axillary shoots.

The new cultivar was discovered within the progeny of a cross made by Robert Glen Barfield on Jan. 3, 2001. EXOTIC ORCHID 'White Knight' was flowered, re-flowered, evaluated and determined to be worthy of production and protection. EXOTIC ORCHID 'White Knight' was submitted by the Inventor to a commercial laboratory, Bangkok Flower Center, in Bangkok, Thailand on Apr. 6, 2004, for propagation through aseptic tissue culture technique. A quantity was produced for evaluation and has demonstrated that the unique combination of characteristics as herein disclosed for the new cultivar are firmly fixed and are retained through successive generations of asexual reproduction.

To my knowledge other seedlings from the same cross that was used to produce EXOTIC ORCHID 'White Knight' are not commercially available from others. The characteristics of EXOTIC ORCHID 'White Knight' are clearly distinguishable from the characteristics of the other plants that were produced.

BRIEF SUMMARY OF THE INVENTION

The following traits have been repeatedly observed and are determined to be basic characteristics of the new cultivar which in combination distinguish this *Brassidium* orchid as a new and distinct cultivar:

Flowers of the new cultivar are star shaped with dark chocolate brown sepals and petals with intermittent cream colored barring, the labellum is white with blood red flecking. The horizontal natural spread is 8.1 centimeters and the vertical spread is 7.8 centimeters.

Inflorescence is a basal spike, approximately 57 centimeters tall with 16 flowers on a first bloom plant.

There are generally four leaves on a mature pseudobulb, two from the base and two from the apex. The apical leaves are from 24 to 35 centimeters in length and are from 4 to 6 centimeters wide. The basal leaves are from 10 to 17 centimeters long and from 3 to 4.5 centimeters wide.

Plants of the new cultivar have not been observed under all possible environmental conditions. The phenotype may vary with variations in the environment such as temperature, light intensity, day length and nutrition, without any change in genotype.

Plants of the new cultivar differ primarily from plants of the parent cultivars in flower size, inflorescence size and type, overall plant size, rate of growth, and speed to maturation. Perhaps the closest commercial comparison to the new cultivar can be made to Oncidiinae seedling orchids that are genetically heterogeneous, and typically lack uniformity in growth, vigor, plant habit, and flower quality. Since this reference point has inconsistent characteristics, a direct comparison for EXOTIC ORCHID 'White Knight' is not available. The new cultivar is a single genotype asexually propagated via tissue culture; thus, its combined horticultural characteristics mentioned above are uniform and predictable.

BRIEF DESCRIPTION OF THE DRAWINGS

All color references are measured against the Pantone® Color System. Colors and numerical measurements are approximate as plant growth, development and flower qualities depend on environmental conditions and cultural practices such as light, temperature, water, nutrition, among others, without any variance in genotype.

Plants used for this description are 1 to 1½ years in-vivo and grown in 3.5 inch, square plastic pots, grown in a polycarbonate covered greenhouse near Hakalau, Hi., where day temperatures range from 73 to 88 degrees and night temperatures range from 62 to 75 degrees Fahrenheit. Light levels are between 1500 and 2500 foot candles. This information reflects the annual variations for the area.

Botanical Classification:

Name: *Brassidium Golden Gamine* 'White Knight':

Parentage: Seedling selected from a cross of the following plants:

*Seed parent.*—*Brassidium Gilded Urchin* 'Ontano' (unpatented).

*Pollen parent.*—*Oncidium ornithorhynchum* 'Lilac Soap' (unpatented).

Propagation:

*Type.*—Asexual propagation by aseptic tissue culture axillary shoot initiation.

*Time to initiate and elongate shoots in vivo.*—About 250 days.

*Time to produce fully rooted young plants.*—About 400 days.

Plant description: Under appropriate growing conditions, plants of the new cultivar attain a mature size of about 32 centimeters in height (top of leaf plane) and about 25 centimeters in width.

Root description: White with green growing tip, and thick velum covering approximately 2 millimeter in diameter.

Foliage description:

*Arrangement.*—Sympodial growth habit.

*Quantity of leaves per sympodial growth.*—Four.

*Leaf length.*—Ten to 35 centimeters.

*Leaf width.*—Three to 6 centimeters.

*Leaf shape.*—The shape is subulate and lanceolate, texture and substance is smooth, waxy and thin.

*Pseudobulb shape.*—The pseudobulb is a laterally compressed ovoid.

*Pseudobulb length.*—6 to 9 centimeters long and 4 to 5.5 centimeters wide.

*Foliage color.*—The foliage color, both top and bottom of the leaf, is Pantone 370 C (green). The pseudobulbs vary from 377 C to 370 C (green). The colors are consistent with no contrasting venation color noted.

*Inflorescence description.*—Inflorescence is a basal spike, approximately 57 centimeters long with approximately 16 flowers on the first bloom.

*Flower arrangement description.*—The flowers are arranged with every other flower facing the opposite direction.

*Flower description.*—Flowers of the new cultivar are star shaped with dark chocolate brown sepals and petals with intermittent cream colored barring, the labellum is white with blood red flecking. The horizontal natural spread is 8.1 centimeters and the vertical spread is 7.8.

*Flower dimensions.*—Sepals are 1.1 centimeters wide and 4.5 centimeters long. Petals are 1 centimeters wide and 4.3 centimeters long. The labellum is 2.5 centimeters wide and 4 centimeters long.

*Flower coloration.*—The sepals and petals are Pantone 4705 C (brown) with intermittent baring of Pantone 134 C (cream). The labellum is white with Pantone 484 C (red) flecks and the crest is Pantone 102 C (yellow). Flower quantity on first bloom plant: 16 flowers. Flower longevity: 6 weeks in favorable conditions.

*Flowering season.*—EXOTIC ORCHID 'White Knight' does not seem to have a flowering season. When a growth matures, it flowers. Flowering has occurred at about 8 month intervals once the plant has reached maturity.

*Fragrance.*—A light floral scent is present during the warm daylight hours.

Reproductive organs: The stamens, style and stigmas are fused into a single short structure referred to as the column, possessing one terminal anther with pollen grains united to pollinia, which are covered by an anther cap. The stigma is located under the column behind the pollinia. The ovary is inferior, with three carpels being present.

*Column.*—The column is erect with wings on either side of the stigma, 2 millimeters wide and 4.5 millimeters long.

*Pollinia.*—Two oval masses of pollen are present, about 1.5 millimeters in diameter.

*Stigma.*—The stigma is concave, oval, with high gloss, and sticky.

*Ovary.*—The ovary is about 3.2 centimeters long and 3 millimeters in diameter.

*Seed.*—Seed production has not been observed.

Disease resistance: Resistance to know pathogens of Oncidiinae has not been observed on plants grown under commercial production conditions.

General observations: Plants of EXOTIC ORCHID 'White Knight' produce a pleasing arrangement of many flowers held on an erect spike. The flowers are long lasting and the plant grows quickly to maturity and blooms.

What is claimed is:

1. A new and distinct variety of orchid plant named EXOTIC ORCHID 'White Knight', substantially as illustrated and described herein.

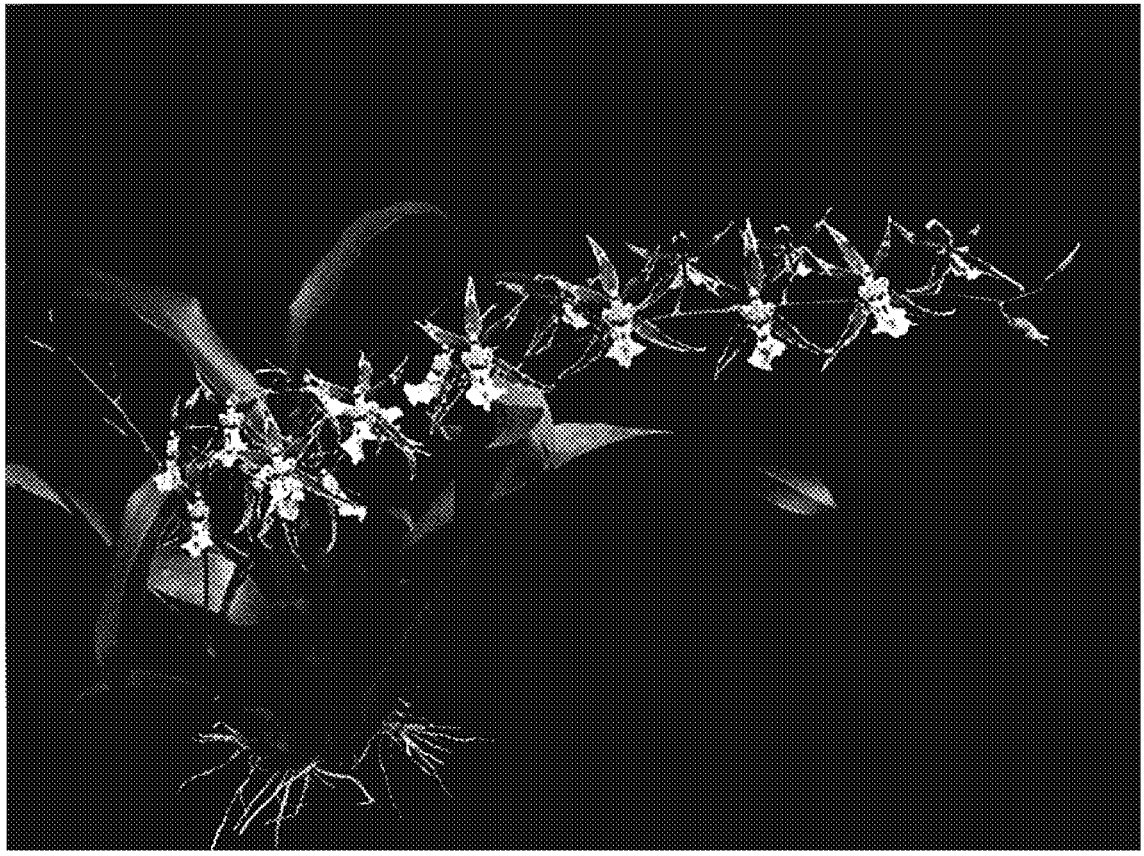

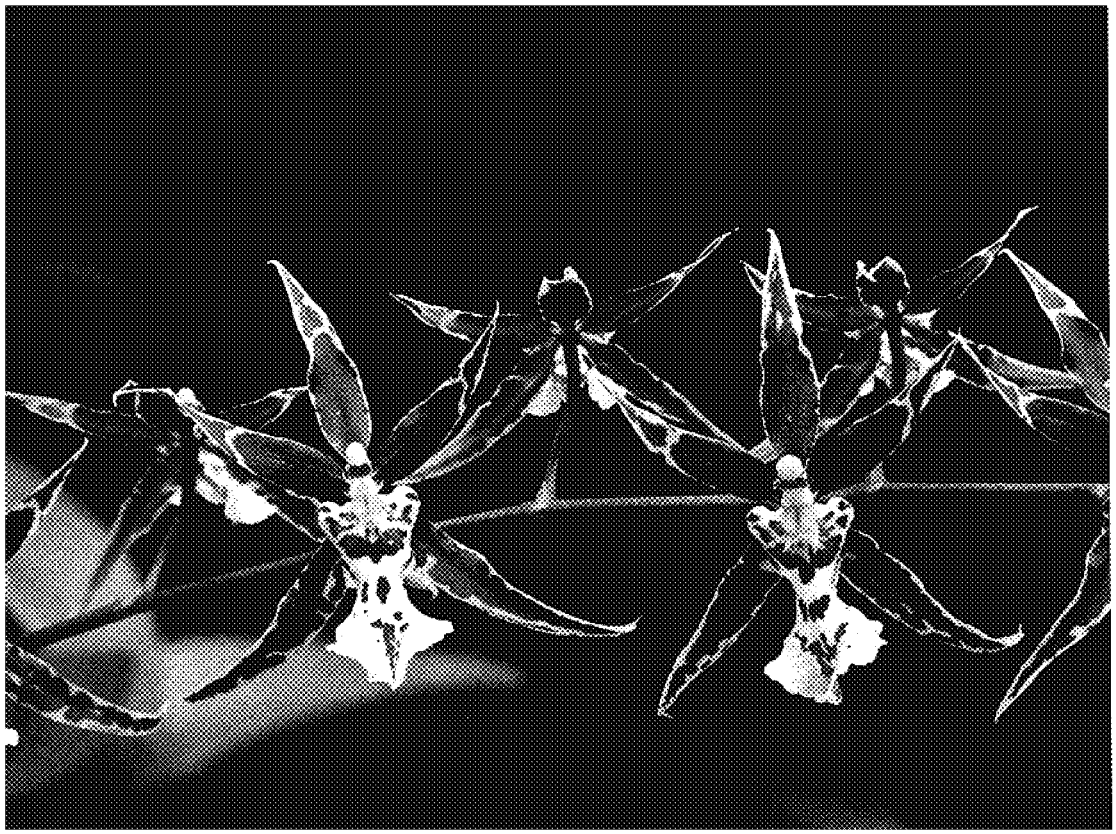

* * * * *